US010921319B2

(12) United States Patent
Gerardos

(10) Patent No.: US 10,921,319 B2
(45) Date of Patent: Feb. 16, 2021

(54) IMMUNOASSAY DETECTION DEVICE WITH TEST STRIP ACCOMMODATED IN A CAPILLARY TUBE

(71) Applicant: Georgios Gerardos, Gateshead (GB)

(72) Inventor: Georgios Gerardos, Gateshead (GB)

(73) Assignee: Great North Research And Innovation Ltd, Newcastle Upon Tyne (GB)

( * ) Notice: Subject to any disclaimer, the term of this patent is extended or adjusted under 35 U.S.C. 154(b) by 798 days.

(21) Appl. No.: 15/202,854

(22) Filed: Jul. 6, 2016

(65) Prior Publication Data

US 2016/0313314 A1    Oct. 27, 2016

(51) Int. Cl.
*G01N 33/558* (2006.01)
*G01N 33/569* (2006.01)

(52) U.S. Cl.
CPC ......... *G01N 33/558* (2013.01); *G01N 33/569* (2013.01)

(58) Field of Classification Search
CPC .......... G01N 33/558; G01N 33/54386; G01N 33/4875; G01N 33/569; B01L 3/5027
USPC ...................................................... 436/514
See application file for complete search history.

(56) References Cited

U.S. PATENT DOCUMENTS

| | | | | |
|---|---|---|---|---|
| 3,941,876 A * | 3/1976 | Marinkovich | ..... | A61B 10/0035 436/513 |
| 4,248,973 A * | 2/1981 | Kallies | ..... | C12Q 1/58 422/423 |
| 4,281,062 A * | 7/1981 | Kallis | ..... | C12Q 1/54 422/565 |
| 4,834,946 A * | 5/1989 | Levin | ..... | G01N 33/5302 422/527 |
| 5,447,837 A * | 9/1995 | Urnovitz | ..... | G01N 33/54386 435/5 |
| 5,656,502 A * | 8/1997 | MacKay | ..... | B01L 3/5023 422/412 |
| 5,759,794 A | 6/1998 | Levine | | |
| 7,378,054 B2 * | 5/2008 | Karmali | ..... | A61B 10/0096 422/410 |
| 8,257,276 B2 * | 9/2012 | Perez | ..... | A61B 5/14514 600/583 |
| 2002/0004246 A1 * | 1/2002 | Daniels | ..... | G01N 33/558 436/514 |
| 2006/0019406 A1 | 1/2006 | Wei et al. | | |
| 2006/0088818 A1 | 4/2006 | Beynon et al. | | |

(Continued)

FOREIGN PATENT DOCUMENTS

EP    1710583 A2    10/2006
WO    8900290 A1    1/1989

(Continued)

OTHER PUBLICATIONS

Oxford English Dictionary, Definition for "around", retrieved from https://www.oed.com/view/Entry/10934?redirectedFrom=around &print on Oct. 30, 2019 (22 pages total) (Year: 2019).*

(Continued)

*Primary Examiner* — Christine Foster
(74) *Attorney, Agent, or Firm* — Fulwider Patton LLP

(57) ABSTRACT

The present invention relates to a detection device for safe and convenient immunoassay of an analyte containing pathogens.

10 Claims, 13 Drawing Sheets

(56) References Cited

U.S. PATENT DOCUMENTS

2007/0178606 A1* 8/2007 Imoarai ................ B01L 3/5082
                                                             436/518
2013/0183658 A1   7/2013 Bamhizer
2014/0206956 A1*  7/2014 Rabinovitz ...... G01N 33/54386
                                                             600/302

FOREIGN PATENT DOCUMENTS

| WO | 9307802 A1 | 4/1993 | |
|---|---|---|---|
| WO | 1996019731 A2 | 6/1996 | |
| WO | 1999000655 A2 | 1/1999 | |
| WO | WO 1999/000655 A2 * | 1/1999 | |
| WO | 2000025135 A1 | 5/2000 | |
| WO | WO 2000/025135 A1 * | 5/2000 | ........... G01N 33/543 |
| WO | 2008118400 A1 | 10/2008 | |
| WO | 2009029073 A1 | 3/2009 | |
| WO | 2013170048 A1 | 11/2013 | |
| WO | WO-2014153308 A2 * | 9/2014 | .............. B01L 3/021 |

OTHER PUBLICATIONS

UK Intellectual Property Office, Search Report in Application No. GB1409093.0, dated Nov. 11, 2014.

\* cited by examiner

Ⓨ Labelled microorganism-specific Ab

Unbound labelled-Abs

Washing solution

IMMUNOASSAY DETECTION DEVICE WITH TEST STRIP ACCOMMODATED IN A CAPILLARY TUBE

CROSS-REFERENCES TO RELATED APPLICATIONS

This application claims priority from United Kingdom Application No. 1409093.0, filed Jan. 5, 2014, incorporated by reference in its entirety.

BACKGROUND

The present invention relates to an immunoassay detection device for detecting a plurality of different targets (eg target ligands such as pathogens, cells, inorganic or organic molecules) in a single sample (eg in a sample of a bodily fluid such as blood).

Infections are one of the main reasons for hospital admission. Depending on the degree of infection, sepsis may be diagnosed. Sepsis is the circulation of infectious bacteria in the blood stream together with their toxins. It is a life threatening condition and urgent treatment is required.

A first diagnostic test for sepsis is the C-reactive protein (CRP) blood test. CRP is a marker that increases when there is an inflammatory response in the body. However this method is not specific. Another cause of inflammation may increase CRP levels in the blood (for example postoperatively) with a risk that the diagnosis of infection is masked or delayed. The method also suffers from time lag because CRP levels in plasma begin increasing 4 to 6 hours after initial tissue injury and/or infection and continue to increase several fold over 24 to 48 hours. In other words, if a patient is infected today, the CRP levels will first indicate infection tomorrow (in 24 hours).

A second diagnostic test is the blood culture test which to date is the most specific. A sample of blood is placed in a sterile bottle with a nutritional medium for various bacteria and/or fungi to grow. If a pathogen grows in the culture then it is positive and an antibiotic sensitivity test may be used to detect the type of antibiotic(s) to which the pathogen is most sensitive. A clinician can then arrange for appropriate therapy. It is normally considered that the worse the infection, the more bacteria will be in the blood stream and consequently the quicker the growth will show in the culture. Except when the number of bacteria in the blood is very high and incompatible with life, the cultures show growth in 24 to 48 hours or longer. For example blood cultures for bacteria are considered negative if they do not show growth after 5 days of incubation. For some types of bacteria and other organisms, the duration can be even longer. In the interim, a patient who is suspected to be septic is treated with a broad spectrum antibiotic which affects adversely other beneficial bacteria in the body. Such antibiotics may also have little or no effect on the pathogenic organisms.

Infections may also be detected by polymerase chain reaction (PCR) techniques. PCR is used mainly in detecting viruses in patient samples and it can provide results in a few hours. Due to its high cost, it is used only when there is a strong suspicion of viral infection or for detection of specific bacteria that are hard to grow in culture.

Immunoassay for small analytes is known and has been applied to larger pathogens such as bacteria. Conventional solid phase surface assays (eg dipstick or test strip assays) present an entire capture surface to the analyte and apply the probe in a separate step. They are suitable for detecting larger pathogens but are slow to respond, need extended incubation times and tend to be inconvenient. With infectious and hazardous samples such as septic blood, they require careful handling in controlled conditions.

Lateral flow immunoassay formats are disadvantageous for larger pathogens (such as microorganisms, bacteria and fungal spores) which tend to move less quickly through an absorbent matrix. For example, they may fail to bind to a probe ligand mobilised from an absorbent assay pad by liquid from the analyte. The liquid tends to flow ahead of the pathogens which fail to be captured by an immobilised antibody in the capture band region. Hence a false low or negative result is sometimes obtained.

US-A-2013/0183658 discloses a device for rapid detection and identification of one or more live target microorganisms in a liquid sample or grown on plates containing solid nutrient media. This device has the disadvantage that the analyte and labelled probe ligands have to be premixed and captured onto a membrane.

WO-A-2008/118400 discloses a technique for rapid detection and identification of colonies or micro-colonies of microorganisms after several hour's growth on light pellucid, molecule-permeable membranes installed on solid nutrient media. The technique suffers from long assay times.

US-A-2006/019406 discloses a lateral flow assay device for detecting the presence or quantity of an analyte residing in a test sample where the lateral flow assay device has a porous membrane in communication with a conjugate pad and a wicking pad.

US-A-2006/0088818 discloses a method of detecting the presence of selected microorganisms within a fluid and includes filtering the fluid to remove large particles prior to analysing the fluid with an antibody matrix. After initial detection and readout, secondary antibodies are added to allow for a second detection step which is inconvenient and time consuming.

EP-A-1710583 discloses a dipstick for testing for the presence of a plurality of different targets in a sample solution. The dipstick has a plurality of different capture zones immobilised to each of which is a different capture moiety. Each capture moiety is capable of capturing a different target. A plurality of different detection probes is provided so that each probe is capable of binding to a different target. Each probe is labelled with (or enables the formation of) a detection signal so that the presence of each target is indicated by the formation of a signal at the capture zone for that target. The target for at least two of the capture moieties is a disease causing micro-organism or a marker indicating the existence of a disease, disorder or condition of the host from which the sample solution was derived. At least two of the capture moieties are capable of binding to different components or markers of the same disease causing microorganism as targets for those capture moieties.

U.S. Pat. No. 5,759,794 discloses a method of assessing patient health by centrifuging blood samples in a transparent tube which contains floats, inserts, liposomes or plastic beads of different densities. Each density-defined body carries analyte-capture binding materials such as antigens or antibodies which are specific to an epitope or other specific high affinity binding site on a target analyte in (for example) blood. The level of analyte is indicative of patient health. However the method is time consuming and unwieldy and requires careful operator handling.

WO-A-00/25135 discloses a two-step capillary flow immunoassay where a first sample is applied using a biotinylated antibody specific to the analyte to a wicking strip to flow to an immobilised immunoreactant which is either antibody specific to the analyte or is the analyte. The biotinylated antibody is premixed with analyte, binds to target species, then avidin/label is added in a lateral flow format. This device allows efficient incubation of a larger pathogen with label but again requires liquid phase pre-mixing of analyte with the detection antibody which is unwieldy and undesirable in the case of a hazardous analyte.

Each of WO-A-2013/170048, WO-A-2009/029073, WO-A-99/00655, WO-A-96/19731, WO-A-93/07802 and WO-A-89/00290 discloses a device for detecting analytes in bodily fluids.

It is an object of the present invention to overcome certain disadvantages in prior art immunoassays (including immunoassays for larger pathogens such as microorganisms, bacteria and fungal spores) by providing a safe and convenient detection device for performing a sandwich immunoassay in an updated and more rapid manner.

SUMMARY OF THE INVENTION

According to an aspect of the present invention there is provided a detection device for detecting one or more pathogens or markers in an analyte comprising:

a test strip including a major surface on which two or more discrete test zones are defined, a first test zone of the two or more discrete test zones having immobilised on or within it a first capture ligand adapted to bind to a first capture target on a first pathogen or marker and a second test zone of the two or more discrete test zones having immobilised on or within it a second capture ligand adapted to bind to a second capture target on a second pathogen or marker, wherein the first pathogen or marker and the second pathogen or marker are the same or different, wherein in use the test strip contacts a detection solution which includes a labelled probe adapted to bind to a probe target on one or more of the pathogens or markers.

The analyte may be a bodily fluid such as blood (or a component thereof), urine, saliva, or cerebrospinal fluid (CSF). The detection device may be used to detect cells, inorganic or organic molecules or other target ligands of interest in the analyte. The detection device may be used for healthcare or environmental purposes.

The pathogen may be a disease-causing agent such as a microorganism, a bacterium, a virus, a protein, a fungus, a parasite or a fungal spore. The marker may be a component or fragment of a pathogen such as an antigen or a species produced by a pathogen or by the body in response to a pathogen and indicative of its presence (for example a protein, a metabolite, a toxin, a cytokine or an antibody).

Preferably the first pathogen or marker and the second pathogen or marker are different.

Preferably the first pathogen or marker and the second pathogen or marker are the same.

Preferably each of the two or more discrete test zones has immobilised on or within it a capture ligand adapted to bind to a capture target on a different pathogen or marker.

In a first preferred embodiment, the second test zone is adjacent to the first test zone in a side-by-side pairing which spans the width of the major surface. Particularly preferably the two or more discrete test zones are a plurality of parallel side-by-side pairings which span the width of the major surface. Typically in this embodiment, the first pathogen or marker and the second pathogen or marker are different.

In a second preferred embodiment, each of the two or more discrete test zones spans the width of the major surface. Typically in this embodiment, the first pathogen or marker and the second pathogen or marker are the same.

Having the first capture ligand and second capture ligand specific for a single pathogen or marker serves to increase sensitivity.

The test strip may extend at one end of the major surface into a holding tab.

Preferably the test strip further includes a control zone having immobilised on or within it a probe capture ligand adapted to bind to the labelled probe (eg to a probe ligand). The control zone may span the width of the major surface. The control zone may be parallel and adjacent to the two or more discrete test zones.

The capture ligand is a species adapted to bind to a capture target on the pathogen or marker. The capture ligand may be (for example) an antibody, an immunoglobulin, an aptamer or (where the marker is an antibody) an antigen. The capture ligand may be immobilised on the major surface by techniques known in the art of diagnostic assays (such as for example by a covalent linkage between the ligand and the surface).

Preferably the first capture ligand is a first pathogen specific antibody and the second capture ligand is a second pathogen specific antibody.

The capture target and the probe target may be the same and present on a single pathogen or marker.

The capture target and the probe target may be different and present on a single pathogen or marker.

Preferably the labelled probe is adapted to bind to a first probe target on the first pathogen or marker and a second probe target on the second pathogen or marker. Such a common labelled probe may be used advantageously for detection of multiple pathogens (eg a number of members of a class of pathogen) on a single test strip where the position indicates the type of pathogen or marker that is detected.

Preferably the detection solution includes a first labelled probe adapted to bind selectively to a first probe target on a first pathogen or marker and a second labelled probe adapted to bind selectively to a second probe target on a second pathogen or marker. Separate labelled probes indicate the presence of each of the first pathogen and the second pathogen thereby providing a dual stage detection process.

The labelled probe may be a probe ligand bound to a label such as a visible label, an optical label (such as an absorption or fluorescent label) or a magnetically or electrically detectable label. The measured intensity of the labelled probe indicates the concentration of pathogen or marker within the analyte.

One of the two or more test zones may have immobilised on or within it multiple capture ligands. This permits detection of multiple pathogens or markers within a single test zone.

Preferably the major surface is substantially planar.

Preferably the test strip is substantially cuboidal.

Preferably the test strip is mounted snugly within a housing to form a self-supporting test device. The housing may take the form of an open tray extending at its end into a grip.

Preferably the test strip is sufficiently flexible to be accommodated resiliently into a capillary tube to form a self-supporting test device. The capillary tube may be cylindrical. The test strip may line the inner cylindrical wall of the capillary tube. For example, the test strip acts as a membrane on the inner cylindrical wall.

The detection device may further comprise a container comprising a closable volume adapted to house the test device and to receive an analyte such that the analyte contacts the major surface. The test device may be selectively removable from the container.

The container may be a cylindrical container. The container may have a wall, a first end, a second end and an internal space to receive an analyte. The test device may be provided within the internal space such that the major surface is spaced apart from the wall. The container may include an opening at its first end that is closed by a septum. In use, an analyte is introduced via the septum and allowed to incubate on the test device to allow binding to take place. The container may include a cap at its second end which is selectively openable to remove the test device. The container may comprise means to re-seal the cap once the test device has been removed.

The container and test device together allow safe, convenient and contamination-free introduction, agitation and extended incubation of an analyte and are especially suited to allow larger pathogens or markers sufficient time to bind to capture ligands.

The housing may interfit removably with the container to position the test device within the internal space.

The test device may form a seal to the opening of the container at the second end such that sample is retained within the container while the test device is being removed.

The detection device may further comprise a reader (eg an optical or fluorescence reader) adapted to measure the amount of bound labelled probe. The reader may include a microscope, a digital camera or a spectrophotometer.

The container may include an anticoagulant (eg on an inside surface).

The interior of the container in use may be at a pressure below atmospheric pressure such that sample is drawn into the container.

The container may have a volume tailored to the anticipated volume of analyte. For use with (for example) blood the container may have a larger sample volume than for use with cerebrospinal fluid. The volume may be 100 ml or less (eg between 20 ml and 50 ml or between 5 ml and 20 ml). Preferably the volume is between 2 ml and 5 ml, most preferably between 0.5 ml and 2 ml (eg 2 ml).

Preferably the detection device further comprises a circuit tube arrangement providing a sample flow path between an inlet and an outlet, wherein the test strip is selectively mountable in the sample flow path adjacent to a second capillary tube.

The detection device may further comprise an apparatus for detection and/or measurement of the concentration of a pathogen and/or marker. The apparatus may comprise: automated means for handling the test device, for exposing the test device to one or more samples, for administering a washing liquid and detection solution and for reading the test device.

The incubation time for the analyte may be 1 to 60 minutes dependent on the type of pathogen and marker. Typically the incubation time for the analyte is 2 to 30 minutes (eg 5 to 15 minutes). The incubation time for the detection solution may be 1 to 15 minutes (eg 2 to 10 minutes).

A capture target or probe target may be a binding site such as a protein, antigen, glycoprotein or region thereof present on the surface of a pathogen or forming part of a marker to which a capture ligand or probe ligand may bind.

A probe capture ligand may be (for example) an antibody or aptamer that binds the probe ligand.

Antibodies may be Ig, monoclonal, polyclonal or synthetic such as aptamers or any other affinity molecules/reagents designed to bind to a ligand.

Embodiments of the invention will now be described by way of example only and with reference to the Figures in which:

DETAILED DESCRIPTION OF THE PREFERRED EMBODIMENTS

First Embodiment

Figure 1:
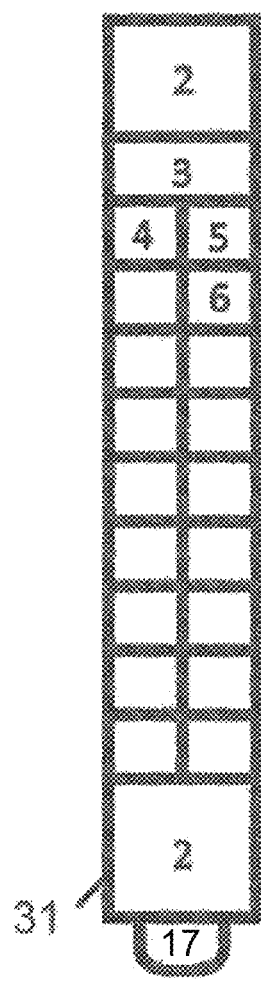
FIG. 1 is a schematic plan view of a test strip of a first embodiment of a detection device according to the invention.
Figure 2:
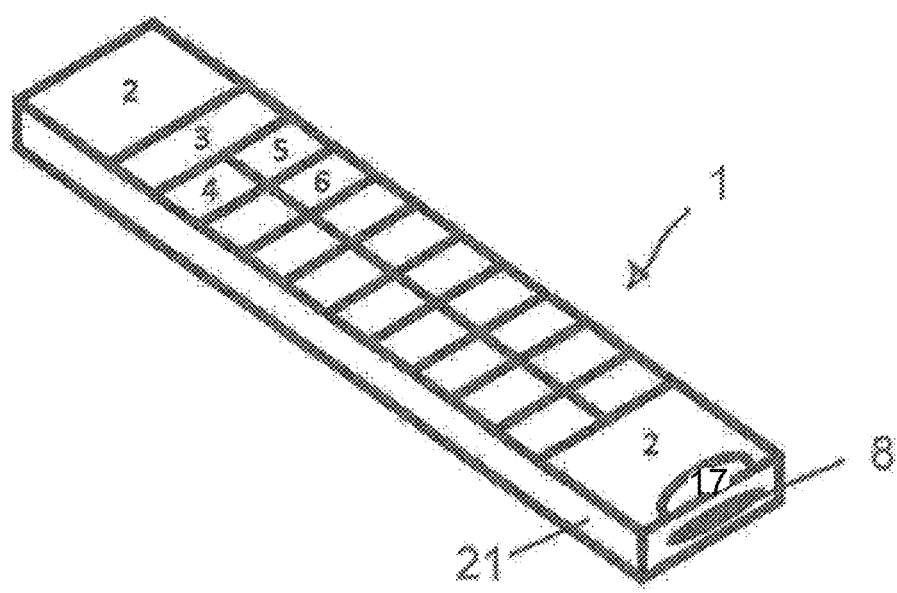
FIG. 2 is an isometric view of a test device comprising the test strip of FIG. 1 mounted in a housing.
Figure 3:
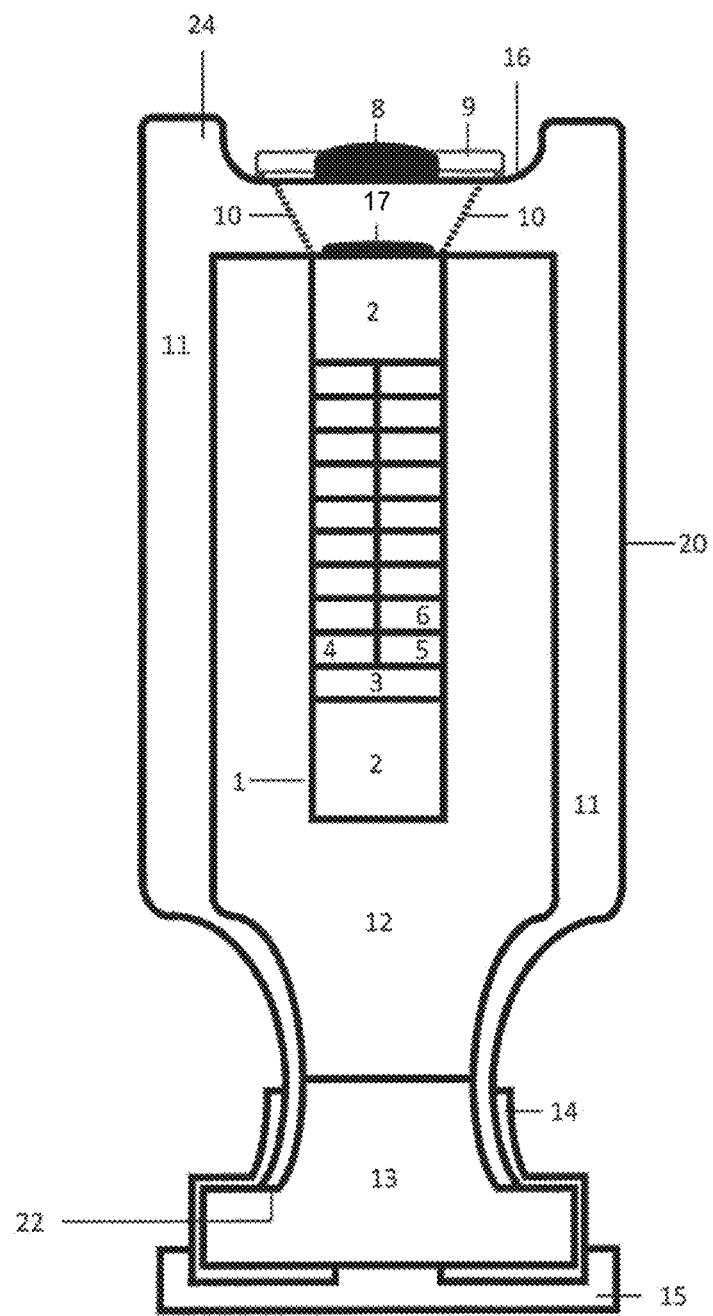
FIG. 3 is a plan view of a container with the test device of FIG. 2 in place.
Figure 4:
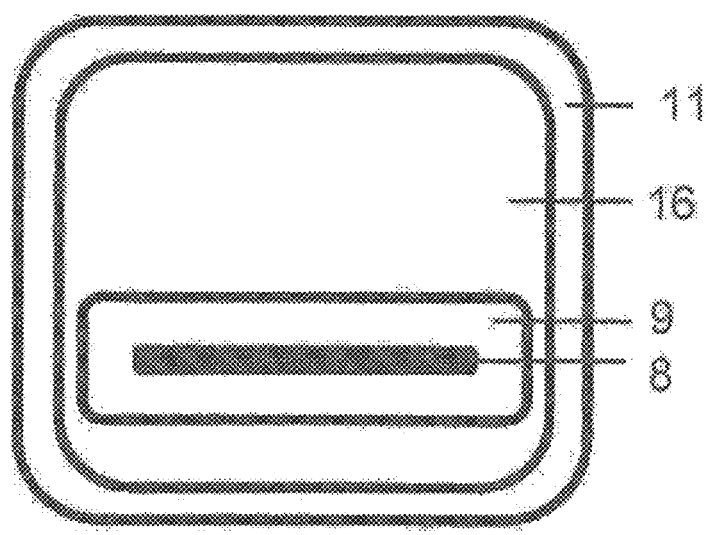
FIG. 4 is a view of a second end of the container shown in FIG. 3.
Figure 5:
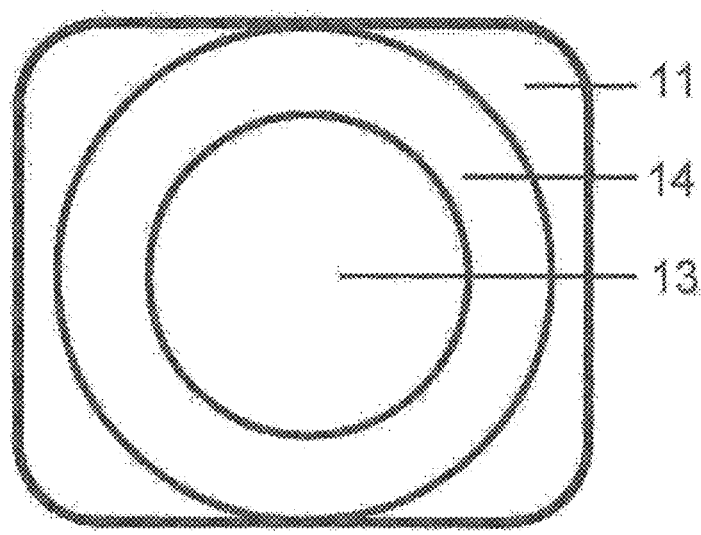
FIG. 5 is a view of a first end of the container shown in FIG. 3.
Figure 6:
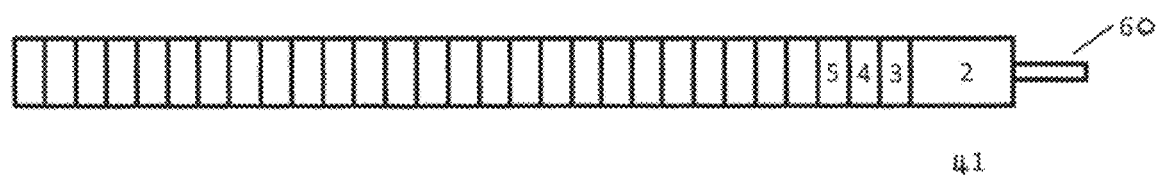
FIG. 6 is a schematic plan view of a test strip of a second embodiment of a detection device according to the invention.
Figure 7:
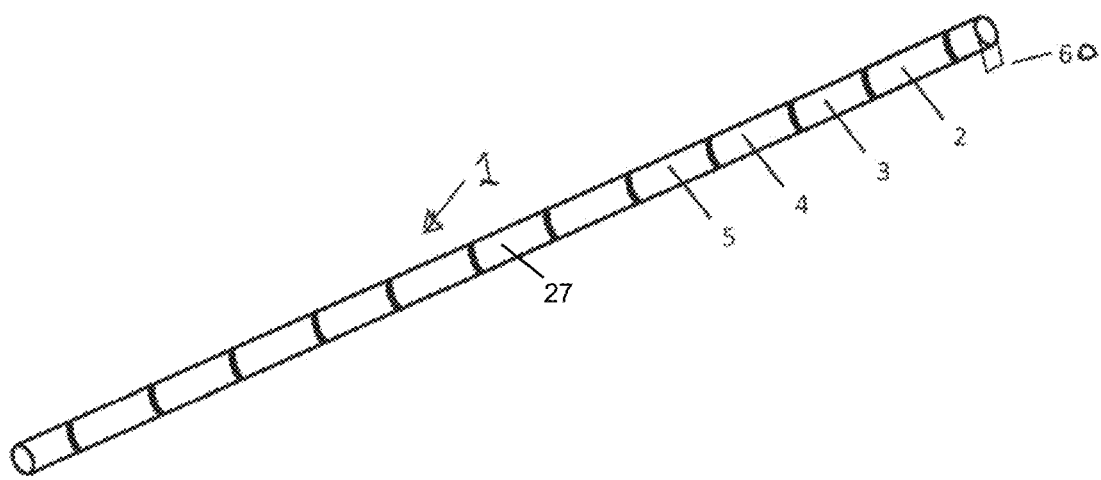
FIG. 7 is an oblique view of a test device comprising the test strip of FIG. 6 accommodated in a capillary tube.

FIGS. 1 to 5 show the elements of a first embodiment of a detection device according to the invention. The detection device includes a substantially cuboidal test strip 31 mounted snugly within a housing 21 to form a self-supporting test device 1. The housing 21 takes the form of an open tray extending at its end into a grip 8.

The test strip 31 has a substantially planar major surface 2 comprising discrete test zones in side-by-side pairings which span the width of the major surface 2. A first test zone 4 has immobilised on it, a first capture ligand adapted to bind to a first capture target on a first pathogen or marker. A second test zone 5 is adjacent to the first test zone 4 in a side-by-side pairing which spans the width of the major surface 2. The second test zone 5 has immobilised on it, a second capture ligand adapted to bind to a second capture target on a second pathogen or marker. A control zone 3 spanning the width of the major surface 2 has a probe capture ligand immobilised within it. The test strip 31 extends at one end of the major surface 2 into a test strip holding tab 17.

The detection device further comprises a cylindrical container 20 having a wall 11, a first end 22, a second end 24 and an internal space 12 to receive an analyte. The housing 21 interfits removably with the container 20 to position the test device 1 within the internal space 12 such that the major surface 2 of the test strip 31 is spaced apart from the wall 11. The container 20 comprises an opening at its first end 22 closed by a septum 13 and a cap 9 in a recessed region 16 of the second end 24 openable to remove the test device 1. The container 20 is sealed by the septum 13 and a rubber seal 10 provided around the sealing surface of the cap 9. The septum 13 is protected by a foil closure 14 and a sterile plastic cap 15 that is removed before use. Sample is injected into the container 20 through the septum 13 using a short needle to allow injection without contacting the test device 1.

The container 20 is typically formed from moulded polymer such as polystyrene or cyclic olefin copolymer. The container 20 has a volume of 2 ml and an intended sample size of 1 ml. An anticoagulant is provided on an inside surface of the wall 11 of the container 20. During use the interior of the container 20 is at a pressure below atmospheric such that sample is drawn into the container 20.

A method of use of the detection device comprises:
removing the cap 15
introducing an analyte into the container 20 by means of injection with a syringe through the septum 13
allowing the analyte and test device 1 to be in contact for an incubation time
holding the test device 1 by the grip 8 provided on housing 21
removing the test device 1 from the container 20 through the cap 9
removing the test strip 31 from the housing 21 by means of the test strip holding tab 17
washing the test strip 31 with a wash solution
exposing the test strip 31 to a detection solution comprising a labelled probe for an incubation time in (for example) a PCR tube or similar container
washing the test strip 31 in a wash solution and
observing the test strip 31 for bound labelled probe.

Figure 10:
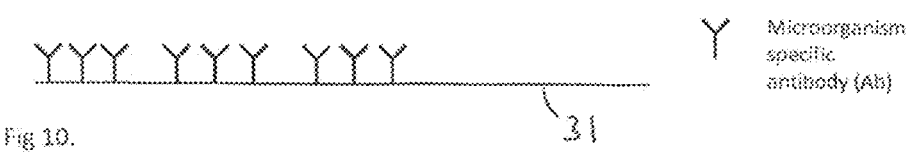
FIGS. 10 to 19 illustrate steps in a process that is performed by an automated system.
Figure 11:
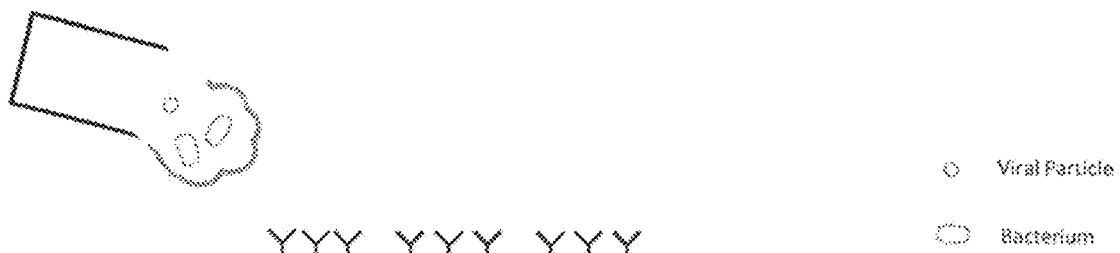
Figure 12:
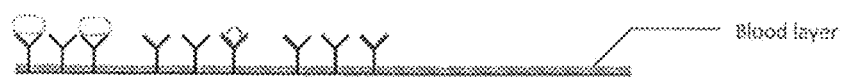
Figure 13:
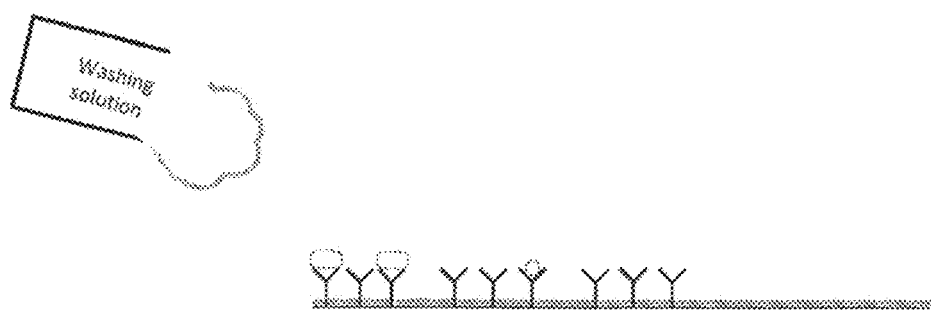
Figure 14:
Figure 15:
Figure 15:
Figure 16:
Figure 17:
Figure 17:
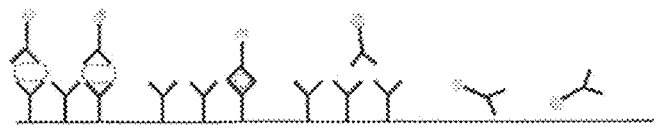
Figure 18:
Figure 19:
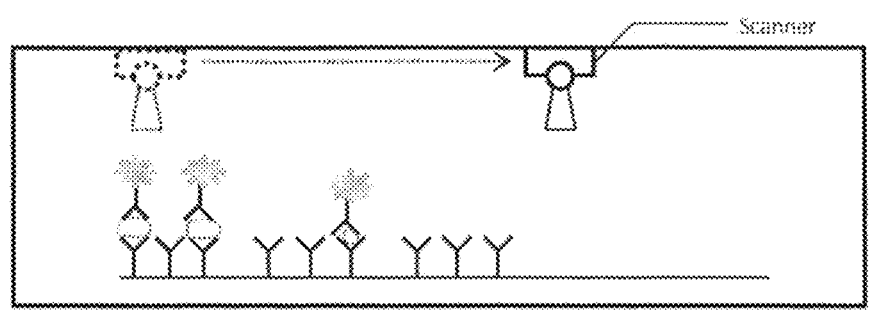

FIGS. 10 to 19 illustrate steps in a process that is performed by an automated system. FIG. 10 shows a test strip 31 to which is attached microorganism-specific antibodies (Abs). FIG. 11 shows a blood sample coming into contact with the test strip 31. The blood sample has multiple microorganisms including bacteria and viral particles. FIG. 12 shows how microorganisms have attached to their microorganism-specific Abs. FIG. 13 shows how a test strip 31 is then washed to remove blood residues. FIG. 14 illustrates a clean test strip 31 with the microorganisms attached to their microorganism-specific Abs. FIG. 15 shows a detection solution with labelled microorganism-specific Abs contacting the test strip 31. The labelled microorganism-specific Abs bind to probe targets on each of the multiple microorganisms and represent a common labelled probe. FIG. 16 shows labelled microorganism-specific Abs attached to their microorganisms. FIG. 17 shows the test strip 31 being washed to remove unbound labelled microorganism-specific Abs. FIG. 18 shows that only labelled microorganism-specific Abs bound to microorganisms are now present on the test strip 31. Finally the test strip 31 is scanned in a scanning system to detect the quantity and physical position of the labelled microorganism-specific Abs (see FIG. 19).

Figure 20:
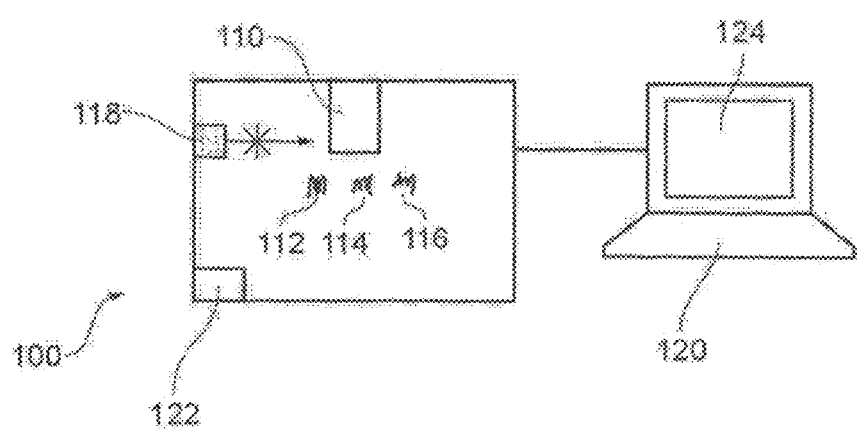
FIG. 20 is a schematic view of a scanning system.

FIG. 20 shows a schematic view of a suitable scanning system 100 having a specimen receiving means 110 adapted to receive test strips 31 (or receptacles containing the test strips 31), a series of sensors 112, 114 and 116, a laser source 118, a control means 120, a memory 122 and an output display 124.

Benefits of the first embodiment of the detection device of the invention include:
1. Rapid detection of an infecting microorganism—in minutes compared to a current minimum of 24 to 48 hours.
2. Smaller blood samples.
3. Earlier use of specific antibiotics.
4. Less use of broad spectrum antibiotics.
5. Less development of resistant strains.
6. Less effect on commensal bacteria flora.
7. Less spending on non-specific treatment.
8. Less possibility of comorbidities and mortalities due to infection as a specific treatment can be commenced earlier.
9. Faster recovery from infections.
10. Less hospitalisation time.
11. Less possibility of contracting hospital acquired infections.
12. Less expense to the healthcare system.

Second Embodiment

FIGS. 6 to 9 show the elements of a second embodiment of a detection device according to the invention. The detection device includes a substantially cuboidal test strip 41 which is sufficiently flexible to be accommodated resiliently into a capillary tube 27 to form a self-supporting test device 1.

The cuboidal test strip 41 has a substantially planar major surface 2 comprising discrete test zones which span the width of the major surface 2. A first test zone 4 has immobilised on it, a first pathogen specific antibody adapted to bind to a first capture target on a pathogen or marker. A second test zone 5 has immobilised on it, a second pathogen specific antibody adapted to bind to a second capture target on the pathogen or marker. Having the first pathogen specific antibody and second pathogen specific antibody specific for a single pathogen or marker serves to increase sensitivity. A control zone 3 spanning the width of the major surface 2 has a probe capture ligand immobilised within it. The cuboidal test strip 41 extends at one end of the major surface 2 into a squarish holding tab 60. The cuboidal test strip 41 contains markers on an edge to indicate the zone at which a positive reaction occurs.

The cuboidal test strip 41 is covered with anticoagulant which prevents samples (eg blood) from clotting and from interfering with the affinity of the antibodies. The capillary tube 27 will have a diameter and length dependent on the clinical need. However the diameter is typically in the range 20 to 150 mm.

The capillary tube 27 containing the cuboidal test strip 41 is used to obtain a sample and then transferred to a laboratory for processing. The capillary tube 27 is inserted into a machine such as the one shown in FIG. 8 where it is connected via a connector 29 to a replaceable elastic capillary tube 28 containing a second test strip with desired antibodies fixed to it. The capillary tube 28 has similar properties to the capillary tube 27.

The machine has a circuit tube arrangement 13 which extends between an input 11 and an output 12 (see FIG. 9) to allow flow of a sample. The sample flows in direction 101 through the capillary tubes 7 and 8 at a speed sufficient to allow various pathogens to bind to their antibodies. This may be achieved by applying suction, pumping air or other inert solutions via the input 11. The sample is then discharged into a waste container via the outlet 12. The capillary tubes 7 and 8 are washed using a neutral washing solution introduced through inlet 11 to remove any residual sample.

A solution with pathogen-specific labelled antibodies is introduced through input 111 and passed though the capillary tubes 27 and 28 at a speed allowing binding of the pathogen-specific labelled antibodies to the fixed antigens from the sample. Once this is complete, the capillary tubes 27 and 28 are washed using a neutral washing solution introduced through input 111 to remove any unbound pathogen-specific labelled antibodies. The capillary tubes 27 and 28 may then be removed from the machine.

The cuboidal test trip 41 and second strip are collected and placed on a flat surface (e.g., a microscope slide) and inserted into a scanner to scan for bound pathogen-specific labelled antibodies. The results are obtained and processed via a computer attached to the scanner to provide accurate and rapid results to clinicians.

Figure 8:
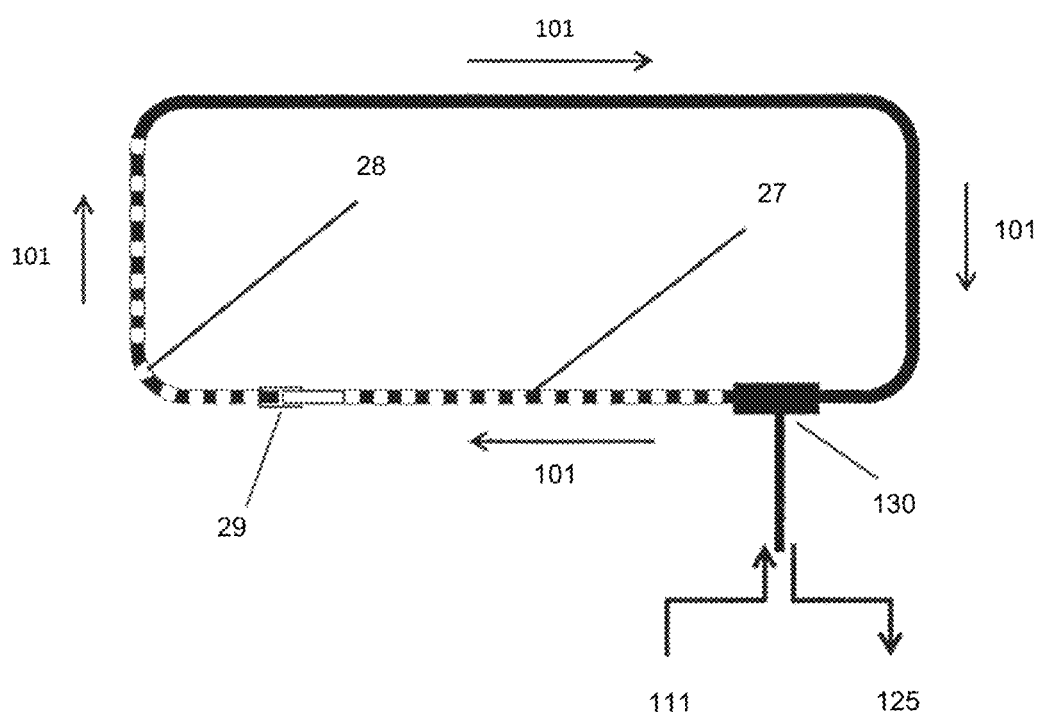
FIG. 8 is a schematic view of a sample being processed in a machine.
Figure 9:
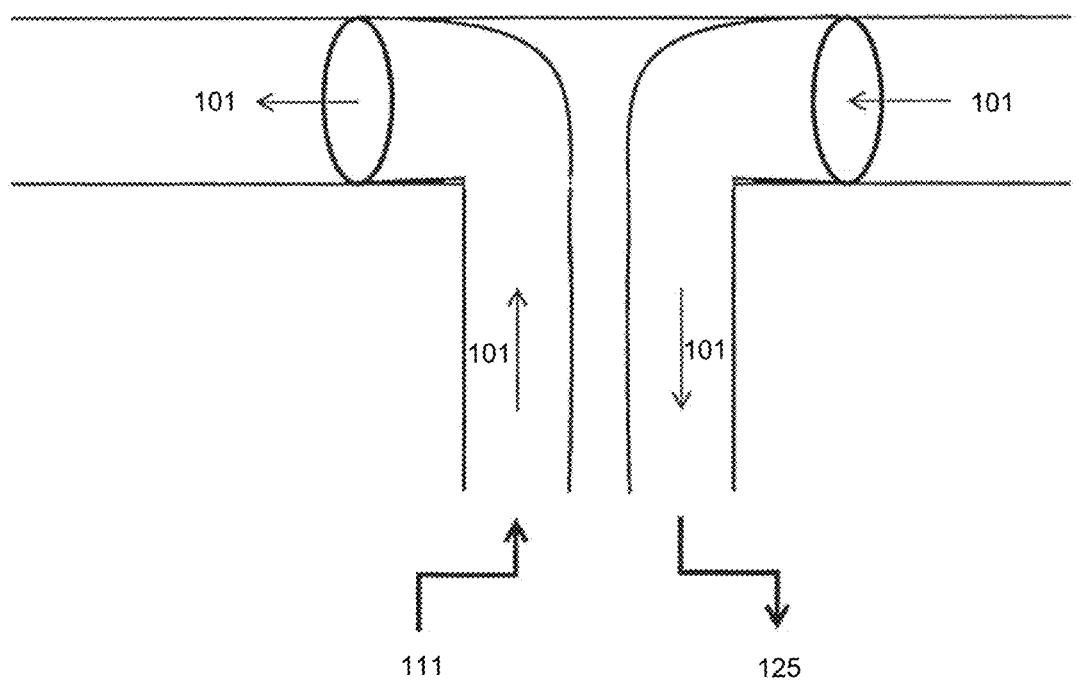
FIG. 9 is a schematic view of a circuit tube arrangement of the machine.

In an alternative embodiment, a scanning system of the type shown in FIG. 20 may be incorporated in the machine shown in FIG. 8 allowing scanning of the capillary tubes 27 and 28 and detection of the results without further handling of the capillary tubes 27 and 28 or test strips.

Benefits of the second embodiment of the detection device of the invention include:

1. It is suitable for smaller samples.
2. It is expected to have higher sensitivity.
3. It has the ability to detect multiple pathogens with low and high organisms-load (higher and lower concentration) in bodily fluids simultaneously.
4. In the automated system, sample processing serves to decrease operator workload and discrepancies that may occur in sample processing, enables simultaneous processing of multiple samples and has low labour costs.

I claim:

1. A method for analysing an analyte using a test device, wherein the test device comprises:
   a capillary tube; and
   a test strip which is flexibly accommodated in the capillary tube and lines the inner wall of the capillary tube, the test strip having:
   a control zone on to which a probe capture ligand is immobilized,
   a first major surface on which two or more test zones are defined,
   a first test zone having immobilised thereon a first analyte specific antibody adapted to bind to a first capture target on a first analyte,
   a second test zone having immobilised thereon, a second analyte-specific antibody adapted to bind to a second capture target on a second analyte, and
   a test strip holding tab, wherein the method comprises the steps of:
   exposing the test device to sample containing the first analyte such that the first analyte becomes bound to the first analyte specific antibody on the first test zone on the test device, washing the test device to remove unbound analyte, exposing the test device to a detection solution comprising at least one labelled probe adapted to bind to the first analyte, washing the test device to remove unbound probe, and observing the presence of bound probe at the first test zone.

2. The method according to claim 1 comprising the step of exposing the test device to a detection solution comprising a labelled probe adapted to bind to probe targets on each of two or more analytes.

3. The method according to claim 1 comprising the step of exposing the test device to a detection solution containing a labelled probe adapted to bind selectively to a probe target on a single analyte.

4. The method according to claim 1 comprising the further steps of: introducing the sample into a container comprising the test device and incubating the sample in contact with the first major surface of the test device and washing the first major surface of the device with a wash solution.

5. The method according to claim 1 comprising the further step of observing the control zone to check that labelled probe has been captured at the control zone.

6. The method according to claim 1 comprising the further step of using a reader to measure the presence or quantity of bound labelled probe.

7. The method according to claim 1 comprising washing the test strip and exposing it to a detection solution comprising a labelled probe.

8. The method according to claim 1 comprising the step of incubating the sample in contact with the first surface of the test device for an incubation time.

9. The method according to claim 8 wherein the incubation time is in the range 1 minute to 1 hour.

10. The method according to claim 8 wherein the incubation time is between 2 and 30 minutes.

* * * * *